United States Patent [19]
Marion et al.

[11] Patent Number: 5,338,518
[45] Date of Patent: Aug. 16, 1994

[54] DISTILLATION-REACTION APPARATUS AND ITS USE FOR CARRYING OUT BALANCED REACTION

[75] Inventors: Marie-Claire Marion, Villeurbanne; Alain Forestiere, Vernaison; Henri Delhomme, Sainte-Foy-Les Lyon, all of France

[73] Assignee: Institute Francais Du Petrole, Rueil Malmaison, France

[21] Appl. No.: 910,380

[22] Filed: Jul. 8, 1992

[30] Foreign Application Priority Data

Jul. 9, 1991 [FR] France ............................ 91 08716
Feb. 4, 1992 [FR] France ............................ 92 01323

[51] Int. Cl.$^5$ .................. B01J 8/02; B01J 8/18; B01D 47/16
[52] U.S. Cl. ...................... 422/211; 422/141; 422/142; 261/94; 203/DIG. 6; 202/158
[58] Field of Search ............ 422/141, 142, 143, 211; 202/158; 203/DIG. 6, 28, 29; 261/94; 428/116

[56] References Cited

U.S. PATENT DOCUMENTS

| | | | |
|---|---|---|---|
| 3,528,783 | 7/1970 | Haselden | 422/211 |
| 3,595,626 | 7/1971 | Sowards | 261/94 |
| 4,133,645 | 1/1979 | Scott | 422/211 |
| 4,232,177 | 11/1980 | Smith, Jr. | 203/DIG. 6 |
| 4,425,285 | 1/1984 | Shimoi et al. | 202/158 |
| 4,439,350 | 3/1984 | Jones, Jr. | 203/DIG. 6 |
| 4,744,928 | 5/1988 | Meier | 428/116 |
| 4,847,430 | 11/1989 | Quang et al. | 203/DIG. 6 |
| 4,917,935 | 4/1990 | Kubicek | 428/178 |
| 5,236,663 | 8/1993 | Alagy et al. | 422/211 |

FOREIGN PATENT DOCUMENTS

| | | |
|---|---|---|
| 0008860 | 10/1985 | European Pat. Off. . |
| 0448844A1 | 10/1991 | European Pat. Off. . |
| 04585472A1 | 11/1991 | European Pat. Off. . |
| 1075613 | 2/1960 | Fed. Rep. of Germany . |
| 1193952 | 11/1959 | France . |
| 1019236 | 2/1966 | United Kingdom . |

*Primary Examiner*—Robert J. Warden
*Assistant Examiner*—Christopher Y. Kim
*Attorney, Agent, or Firm*—Millen, White, Zelano, & Branigan

[57] ABSTRACT

A distillation-reaction apparatus comprises at least one distillation-reaction zone (G,H) having, on a perforated support (5) permitting the passage of fluids at least one element of type J—container (3b) of volume Vt containing a volume Va of solid catalytic particles—and at least one element of type K—(4) of type K1 and/or (3a) of type K2—the element of type K2 being a container not containing solid catalytic particles, the elements having adequate mechanical characteristics to withstand the loading of the elements in the zone and the perforations of the support being sufficiently small to retain the said elements. The apparatus can be used for performing chemical reactions and the fractionation of the reaction mixture, e.g., for the synthesis of ethers from olefins and alcohols.

15 Claims, 2 Drawing Sheets

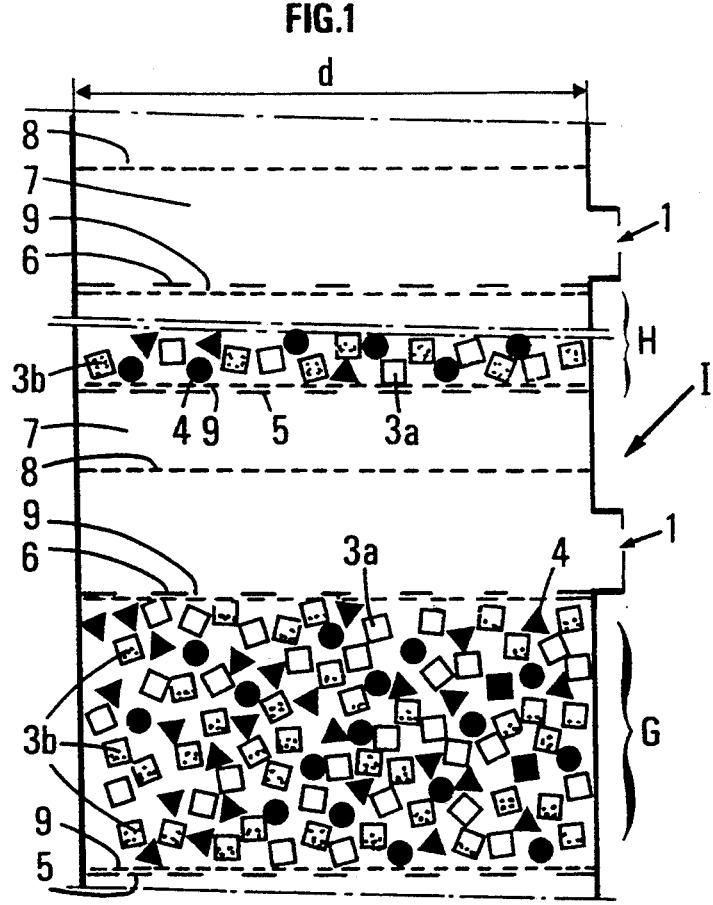

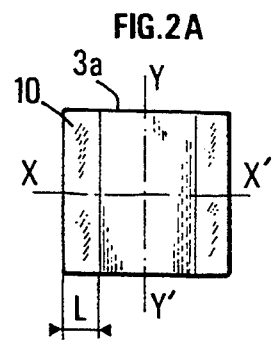
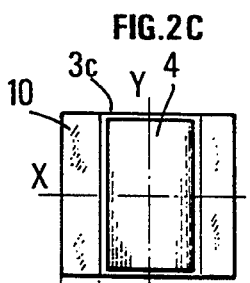
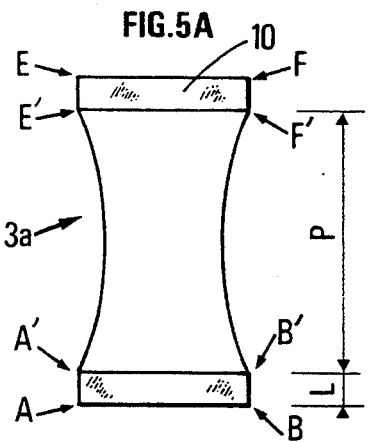
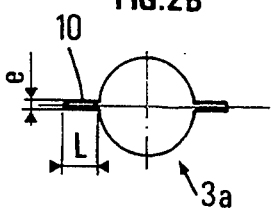
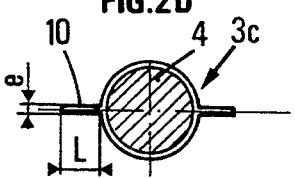
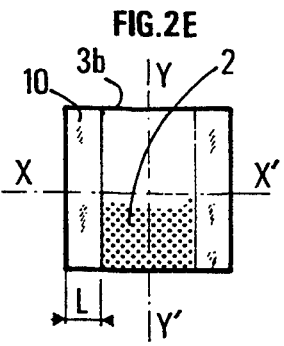
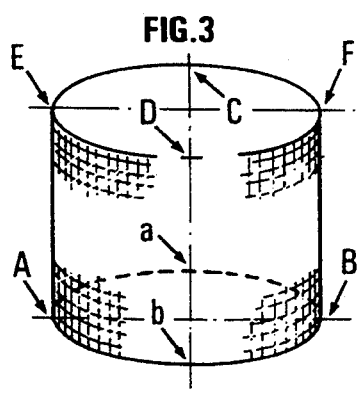
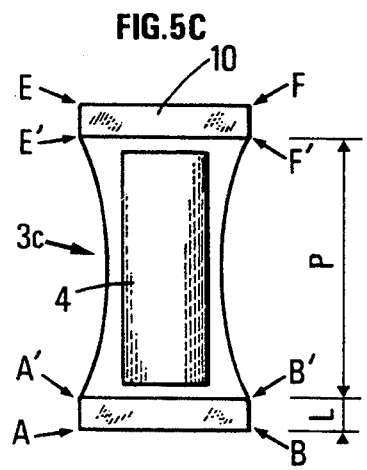
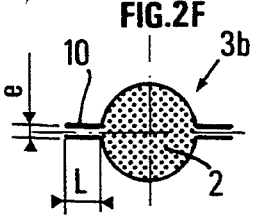
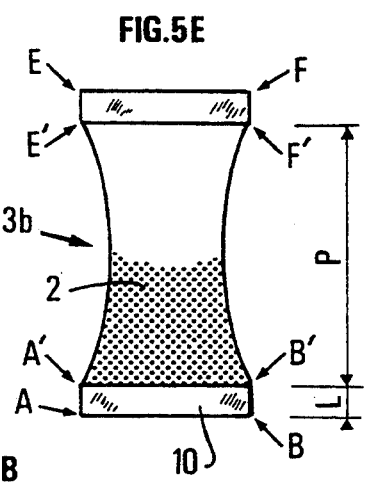
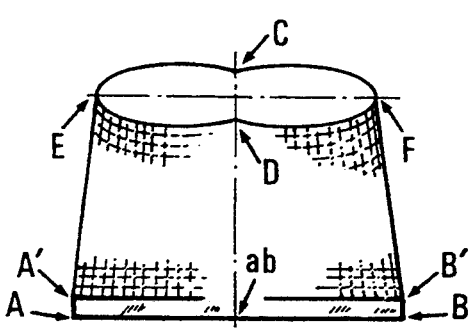
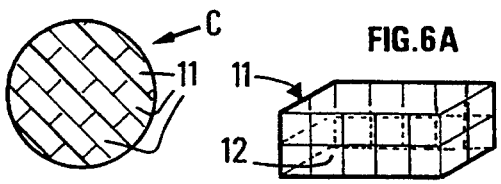

DISTILLATION-REACTION APPARATUS AND ITS USE FOR CARRYING OUT BALANCED REACTION

SUMMARY OF THE INVENTION

The present invention relates to a distillation-reaction apparatus and to its use for performing chemical reactions and the fractionation of the reaction mixture.

It also relates to a process for the preparation of an ether by the reaction of olefins on alcohols, in which concurrently the reaction and the distillation of the products formed take place, more particularly with a view to separating these products from the constituents which have not reacted.

It has been known for sometime that, in the case of a balanced reaction, thermodynamics limits the conversion of the reagents. The introduction of one of the reagents in excess makes it possible to increase the conversion of the other reagents. However, this method is often costly, because it requires a supplementary installation for recovering the reagent introduced in excess.

One way of bringing about an overall conversion beyond the thermodynamic equilibrium is to use the distillation-reactive method. This method consists of carrying out the reaction, normally in the presence of a catalyst, and the distillation in the same enclosure, for separating the products from the other constituents as they form. This method is, e.g., used in the case of etherification reactions (U.S. Pat. Nos. 3,629,478, 4,847,430 and EP-B-8860).

U.S. Pat. No. 3,629,478 proposes the use of distillation trays and of only placing the catalyst in the liquid downflows of said trays, with a view to avoiding any disturbance of the vapor phase through the catalyst. However, the presence of the catalyst in said downflows creates a pressure drop, so that the liquid tends to descend in countercurrent manner in the orifices provided for the passage of the vapor on the working table of each distillation tray. Thus, a significant part of the liquid does not then come into contact with the catalyst, which limits the reaction efficiency of said distillation-reaction apparatus.

U.S. Pat. No. 4,847,430 describes the use of reaction-distillation zones, in which the catalyst bed alternates with the distillation zone. Through said catalyst bed, passages reserved for the vapor phase prevent any gas-liquid contact and limit the pressure drop problems. However, the physical equilibrium between the liquid and the vapor is not permanently achieved, so that in the catalytic zone there can be an exhaustion of one of the reagents. This leads to a loss of efficiency from the reaction standpoint, particularly as the reactive column operates under conditions close to chemical equilibrium.

European Patent 8860 proposes the use of a distillation column filled with an appropriate catalyst for the preparation of methyl tert. butyl ether (MTBE), in which the catalyst, as a function of its shape, also at least partly serves as a packing or lining for the distillation, thus forming the MTBE and separating it at the same time from the other constituents present. However, the overall structure of the packing containing the catalyst and its stacking in the column in the vertical direction is unfavorable to the gas-liquid contact and does not offer a high efficiency level on the distillation plane. Moreover, this type of column packing is expensive, because it includes the cost of the catalyst and that of producing the catalytic packing or lining and to this is added the cost of the metal lattice wound around the catalyst layer. Moreover, when it becomes necessary to replace the catalyst, it is also necessary to replace the metal lattice, which significantly increases the cost of this operation.

According to the description of European Patent 8860 and in particular its claim 6, the catalyst is contained in textile pockets supported by a metal netting intimately associated therewith. According to the description, said netting is necessary to avoid the formation of a very compact bed, which would lead to a very considerable pressure drop in the same way as a loose catalyst bed.

The present invention aims at obviating the disadvantages of the processes and apparatuses used for performing the same described in the prior art, by proposing an apparatus making it possible to perform a balanced reaction beyond the thermodynamic equilibrium in an apparatus having a distillation-reaction zone and making it possible to obtain a very good efficiency both from the reaction and from the distillation standpoints.

The invention consequently relates to a distillation-reaction apparatus having at least one distillation-reaction zone containing, on a perforated support permitting the passage of fluids, at least one element of type J comprising a container containing a quantity of solid catalytic particles such that the volume $V_a$, occupied by all these particles in the said container and measured after their contacting with the charge under the conditions of the reaction, is non-zero and below the internal volume $V_t$ of said container, which has an outer envelope permeable to the fluids and impermeable to the solid catalytic particles, whereby said distillation-reaction zone can also contain at least one element of type K having at least the double function of ensuring a predetermined vacuum level in the distalliation-reaction zone and a distillation effect, said elements of type J and of type K having adequate mechanical characteristics to withstand, without excessive deformation, the loading of all the elements of types J and K present in said distillation-reaction zone, the perforations of said perforated support being sufficiently small to retain said elements of types J and K.

Within the framework of the present description, the term perforated support designates both a plate having adequate mechanical characteristics to support the weight of the elements of types J and K and having perforations permitting the passage of various fluids and sufficiently small to retain or hold back said elements, and an assembly incorporating a plate and a grid, said plate having perforations permitting the passage of various fluids, but insufficiently small to retain or hold back all the elements, said grid having meshes permitting the passage of various fluids and sufficiently small to retain or hold back the smallest of said elements present in the distillation-reaction zone. In the second case, the combination of the grid and plate has adequate mechanical characteristics to support the weight of the elements. The grid and the plate are made from materials which are inert with respect to the different fluids and solids with which said materials come into contact.

In the present description, the term distillation-reaction apparatus designates a piece of equipment in which it is possible to simultaneously carry out a chemical reaction and a fractionation (normally multistage) and the term distillation-reaction zone refers to the zone in which the reaction and fractionation concomitantly take place.

Within the framework of the present description, the elements of type J fulfill the double reaction-distillation function. As a function of their shape and filling procedure, the containers containing the solid catalytic particles at least partly make it possible to control the vacuum level defined in the distillation-reaction zone.

Within the container, the volume Va occupied by all the solid catalytic particles in the reaction condition (i.e., wetted by reagents) of a non-zero nature is below the total internal volume of the container Vt. It is thus possible to determine a filling level ($\sigma 1$) of said container: $\sigma 1 = Va/Vt$. This filling level is normally between 0 and 1, (excluding the limits), preferably between 0 and 0.9 (including the upper limit) and in preferred manner between 0 and 0.8 (including the upper limit) or in an even more preferred manner between 0 and 0.6 (upper limit included). It is also possible to refer to a vacuum level ($\sigma 2$) within said container and which is defined by the relation: $\sigma 2 = (Vt - Va)/Vt$. In all cases the sum $\sigma 1 + \sigma 2$ is equal to 1. The filling level within each container is normally chosen in such a way that the solid catalytic particles are mobile, bearing in mind the movement of the fluids with the gas rising and the liquid falling. Defined in this way and under the operating conditions, each container containing the catalytic particles is considered to contain a fluidized bed of solid catalytic particles.

In the distillation-reaction apparatus according to the invention, as a result of a random stacking (i.e., loose) of the element or elements of type J (i.e., the container or containers containing the solid catalytic particles) and the element or elements of type K and as a result of the mobility of the solid catalytic particles, the liquid and gas flows are disturbed in permanent manner so as to optimize the gas-liquid and liquid-solid contacts (particularly the catalyst). The liquid-gas physical equilibrium is permanently maintained while performing the irrigation of the catalyst in the best possible way. In the distillation-reaction zone, the reaction and distillation functions are concomitant, which gives a maximum efficiency of the reactive column.

Moreover, said plurality of fluidized catalytic beds, due to the presence of the container or containers containing the solid catalytic particles, permits a better dissipation of the calories by eliminating the hot points due to the exothermicity of the reaction and thus increases the life of the catalyst (which is often sensitive to the temperature).

Finally, for a given shape, the value of the filling level of each container containing the solid catalytic particles is adjusted so as to control the volume of the distillation-reaction zone by optimizing the "column dimensioning" and pressure drop parameters.

Within the framework of the present invention, the expression "without excessive deformation" means that the mechanical characteristics of the elements of types J and K are such that, no matter what the position of any random one of these elements in the distillation-reaction zone, it continues to be able to ensure all the functions required of it and in particular with respect to the element or elements of type K to ensure the existence of a non-zero volume free from any catalytic solid, thereby making it possible to obtain a given vacuum level with respect to each element and consequently participating in the obtaining of a predetermined overall vacuum level in the distillation-reaction zone.

In the case where at least one type K element is an empty or nonempty container, if V is the volume of said container after manufacture, the volume V1 of the container within the distalliation-reaction zone is equal to or below V, but without being zero. Preferably use is made of containers manufactured in such a way that, for each container, the volume V1 is very close to V and usually such that each container undergoes no deformation under the weight of the load of all the elements. Thus, in this preferred embodiment, V1 is between 80 and 100% and usually between 90 and 100% of the value V.

In a frequently encountered embodiment of the invention, the distillation-reaction zone comprises at least one and preferably several (i.e., two or more) type J elements and at least one and preferably several type K elements. Thus, said zone has at least one and preferably several type K elements chosen from within the group formed by distillation packing materials, which form type E1 elements, and empty or non-empty containers not containing solid catalytic particles, said empty or non-empty containers forming K2 type elements. The K1 and K2 type elements form two separate subgroups, but having the same functions, of elements of type K.

Various containers forming elements of type K2 can be identical or different from one another, the difference being, e.g., based on their size, shape or material from which they are made.

The different containers of type J containing solid catalytic particles can be the same or differ from one another, e.g., on the basis of their size, shape or material from which they are made. They can also differ on the basis of their filling level $\tau 1$. Usually the distillation-reaction zone has several containers containing solid catalytic particles, which are identical with regards to their size, shape and material from which they are made.

The distillation-reaction zone of the apparatus according to the invention can therefore have, according to a first embodiment, at least one type J element and at least one type K1 element, or according to a second embodiment at least one type J element and at least one type K2 element, or according to another embodiment at least one type J element, at least one type K1 element and at least one type K2 element. It is also possible to envisage other embodiments without passing beyond the scope of the invention.

A distinction is made between two different categories of type K2 elements, the first being constituted by empty containers and the second by non-empty containers containing one or more packing materials.

According to a special embodiment of the invention, according to which the distillation-reaction zone contains type J elements, type K1 elements and type K2 elements, the number of type K2 elements compared with the total number of type K elements (i.e., the total number of elements of type E1 and type K2) is not critical. It is therefore possible to have within the distillation-reaction zone a single type K1 element or a single type K2 element. Frequently, there are 1 to 99% and preferably 1 to 90% of type K elements present in the distillation-reaction zone in one or another of the types (K1 or K2). In this special embodiment, within the distillation-reaction zone there is at least one type K1 element (packing material) or at least one type K2 element (container) and frequently 99 to 1% and preferably 99 to 10% of elements of the same type (K1 or K2), based on the total number of type elements present in the distillation-reaction zone.

The packing materials used in the present invention are chosen as a function of the efficiency required for the distillation function. The term distillation packing material means all known packing materials, such as, e.g., solids in the form of rings, polylobar extrudates or saddles. As non-limitative examples of packing or filling materials usable in the present invention, reference is made to Raschig rings, Pall rings, Intos rings, Berl saddles, Novalox saddles and Intalox saddles. It is also possible to use geometrically regular packing materials such as those developed, e.g., 25 years ago by Sulzer or those described in patents: U.S. Pat. No. 3,679,537, EP-B-70,917, EP-A-212,202, FR-A-2,637,059 and FR-A-2,637,060. Thus, as packing materials are proposed Multiknit-wound knitted pads or even netting fragments. For a description of distillation packing materials, reference can also be made to the New English edition of Ullmann's Encyclopedia of Industrial Chemistry, Volume B3, Unit Operation II, Chapter 4, Distillation and Rectification, particularly pp. 70 to 92.

The elements of type K2 consisting of "non-empty" containers can contain, each independently of one another, one or more packing materials, which can be the same or differ with regards to their size, shape or material from which they are made.

Within the sense of the present invention cases are included where the packing material forms an entity with the container, i.e., when said material and the envelope of the container are integral with one another, such as is, e.g., the case when the packing material is an e.g., a metal lattice or when the envelope and the packing material are made from the same netting or fabric.

The various elements of type K (empty or non-empty containers or packing materials) can be the same as one another or differ e.g., on the basis of their size, shape or material from which they are made. Generally the distillation-reaction zone has several type K2 elements identical as regards size, shape and material from which they are made. According to a preferred embodiment of the invention said elements are empty containers. According to another particularly preferred embodiment a type K1 element is used.

The apparatus according to the invention has many varied applications. It can easily be modified as a function of the particular needs of the envisaged application. Thus, the heterogeneous catalyst is chosen as a function of the reaction involved.

One of the interests of the apparatus according to the invention is that it permits, without any special difficulty, the recycling of the type K element or elements. This recycling can be facilitated, particularly when the type K elements are of type K2, e.g., by using type J and type K2 elements having different sizes or shapes or a means making it possible to facilitate sorting between the type J and type K2 elements. These type J and K2 elements can be containers having, e.g., for each type an envelope with characteristics facilitating sorting. Without inferring any limitation reference can be made to magnetic sorting of containers when use is made of type K elements having a metallic part, or in the case of type K2 elements having a metal envelope made from a metal M1 and type J elements not having a metal part, or not having a metal envelope made from a metal M1, but which can be made from a metal M2 having different magnetic properties to those of the metal M1.

According to the present invention, the closed outer envelope forming any type K2 container, which may or may not contain packing or filling materials, is permeable to fluids, i.e., to liquids and gases, while being impermeable to the other elements present, i.e., to the other containers, to the packing materials located in said container when it is not empty and any packing materials contained in the distillation-reaction zone. Therefore in the case of a non-empty type K2 container, said envelope prevents the packing material or materials from passing out of the container, but allows the passage therethrough of liquids and gases. The packing materials contained in the containers in this way retain their full distillation efficiency.

According to the present invention, the closed outer envelope forming any type J container and containing the solid catalytic particles is permeable to fluids, i.e., to liquids and gases, while being impermeable to solid catalytic particles (catalyst) to the packing material or materials contained in the distillation-reaction zone and to other containers present therein. Therefore the envelope prevents the exiting of solid catalytic particles.

The envelope of any type J container is normally made from a solid material, which can be a permeable or porous material, or even an impermeable material in which openings or pores are provided with a sufficiently small size to keep the solid catalytic particles within the container.

The envelope of the container forming type K2 elements is normally made from a solid material, which can be the same or different from that chosen for producing the containers constituting type J elements. It is therefore possible to use a permeable or porous material, or even an impermeable material in which openings or pores are provided having a sufficiently small size to avoid in the case of containers forming type K2 elements other elements from penetrating the said containers and in the case of non-empty type K2 containers maintaining the distillation packing material or materials within the container. In both these cases, the sizes of the openings of the containers forming type K2 elements are adequate to permit the passage of fluids through said container.

Particularly in the case of containers forming type J elements, it is possible to better define the geometrical characteristics of these openings, although this in no way limits the present invention. In this case, if the smallest dimension of the smallest solid catalytic particle is equal to n meter (m), whereas the largest dimension of the openings permitting the passage of fluids is usually equal to or below $0.9 \times n$ m and preferably equal to or below $0.5 \times n$ m. In principle, there is no limit with respect to the size of the solid catalytic particles or catalyst grains and the lower limit of the smallest dimension of the openings is equal to the minimum dimension permitting the passage of fluids and in particular liquid. In most cases, the distillation-reaction zone contains containers forming type J elements containing catalysts having a grain size between $5 \times 10^{-6}$ m and $2 \times 10^{-1}$ m. In a nonlimitative example, in the case of using an acid catalyst for the synthesis of an ether from an olefin and an alcohol, the catalyst grains usually have a grain size between $1 \times 10^{-4}$ m and $2 \times 10^2$ m. In the most frequent embodiment, the dimensions of the openings are identical for containers of each type present in the distillation-reaction zone and substantially identical between individual containers.

As an example of a material usable for forming the envelope of the containers, reference can be made to woven or non-woven materials. The material usable for forming the envelope of the containers can have a natural, such as mineral, vegetable or animal origin, or even a synthetic origin. Reference is made in the form of non-limitative examples to polypropylene, polyesters, polyamides, aluminum, copper, titanium, nickel, platinum, stainless steel or a metal lattice or netting as appropriate materials, whereby the dimensions of the openings or meshes of said netting or lattice are as defined hereinbefore. The chosen material must be physically and chemically inert relative to the fluids and solids with which it comes into contact.

When the material chosen for forming the envelope of the containers, particularly for those forming type J elements, but also for those forming type K2 elements consisting of empty containers, does not have adequate mechanical characteristics to make it possible to obtain containers able to withstand the weight of all the elements present in the distillation-reaction zone, mechanical reinforcement means are included, such as, e.g., steel rods or any other known means making it possible to produce containers having the desired mechanical characteristics.

In the case of containers forming type K2 non-empty elements, as a function of the selected distillation material or materials, preference is given to the choice of the material constituting the container envelope in such a way that the association of the two makes it possible to obtain an overall lining material-envelope assembly for the container having a certain rigidity, i.e., having an adequate crushing resistance to enable a container located at the base of the distillation-reaction zone not to be crushed by the weight of the elements. Thus, if the distillation packing material is rigid, the envelope can be made from a flexible as opposed to rigid material. Conversely, if the distillation packing material is not very rigid, the envelope is preferably made from a rigid material.

In the case of containers forming type J elements, it is often preferable to use either a relatively rigid material for the container envelope, or use containers having mechanical reinforcing means. As a function of the mechanical characteristics of the catalyst, preference is given to the choice of a container envelope-forming material such that the combination of the two makes it possible to obtain a container envelope-catalyst assembly having a certain rigidity, i.e., having an adequate crushing resistance to enable a container located at the bottom of the distillation-reaction zone not to be crushed by the weight of all the elements of said zone. Thus, if the catalyst is not very friable and/or not brittle, the envelope can be made from a flexible, as opposed to a rigid material. However, if the catalyst is relatively friable and/or brittle, the envelope is preferably made from a rigid material. To avoid any risks of the formation of fines due to the crumbling of the catalyst, it is often preferable to use either a relatively rigid material for the container envelope, or to use containers having mechanical reinforcing means.

The invention permits a good control of the vacuum level in the distillation-reaction zone, a good control of the filling level in said zone and during the use of the apparatus and a good control of the pressure drops. The vacuum level within the distillation-reaction zone can be fixed at a previously chosen value, e.g., obtained by choosing the filling level of each of the containers containing the catalytic particles and the number of type K, i.e., type K1 and/or type K2 elements, included in the distillation-reaction zone. The vacuum level also varies as a function of the filling procedure for the non-empty containers forming the elements of type K2 and the quality and quantity of the distillation packing or filling materials contained in said non-empty container K2.

In a special embodiment of the invention, each container or a certain number of them, has at least one and preferably at least two means having a function of mechanically reinforcing the said container and which can have a secondary function of maintaining a minimum space between said container and the closest container in contact with the end of said means and/or one of the closest solid surfaces in contact with the end of said means. Said means can be in the form of one or more rigid fins or flanges. They make it possible to produce containers having a relatively flexible material envelope, while still having the desired mechanical characteristics. They also make it possible to regulate the vacuum level of the distillation-reaction zone and also permit a good control of the pressure drops. They can also facilitate sorting, e.g., magnetic sorting, of the containers, e.g., those of type K2 not containing solid catalytic particles.

The number, size and quality of the flanges makes it possible to determine the overall mechanical characteristics of the containers and also act on the vacuum level and filling level of the distillation-reaction zone. In the same way, these flanges make it possible to define and modify the pressure drop. The use of containers having flanges and, compared with the use of type K2 empty containers, another way, which may or may not be complementary, of acting on the vacuum level of the distillation-reaction zone. Thus, the larger the size and number of the flanges, the more available space between the containers of the different types and the higher the vacuum level.

These flanges preferably have a significant rigidity. They must have a crushing resistance so as to be able to fulfill their mechanical reinforcement function and possibly the function of reciprocately spacing the containers or spacing the container and the apparatus walls and also the packing materials possibly present in the distillation-reaction zone. These flanges can have a plate, a reinforcement or a reinforcing rod, or can more simply result from the welding or bonding of the envelope ends.

The size of the flange or fin is linked with the size of the container. Its length (L) is usually between approximately $0.01 \times p$ m and $1 \times p$ m and is preferably between approximately $0.05 \times p$ M and $1 \times p$ m, if p designates the largest dimension of the container. The thickness of the flanges can vary considerably. It is usually between $1 \times 10^{-4}$ m and $5 \times 10^{-2}$ m. The number of flanges is not limited and can very, e.g., between 1 and 20 and usually between 2 and 10. In an embodiment of the production of containers having flanges, which is particularly easy to put into effect, they have two flanges.

The largest dimension of the elements present in the distalliation-reaction zone and in particular containers, is normally below 0.1 and preferably below 0.07 times the diameter of the distillation-reaction zone in the most frequent case where the latter has a substantially circular cross-section. However, it is also possible in this case and without passing outside the scope of the invention to use elements, whereof the largest dimension can have a value exceeding 0.1 times the diameter of the distalliation-reaction zone and at the most equal to the diameter of said zone.

Usually the empty containers are made from a material having adequate mechanical characteristics to ensure that it is not vital to include mechanical reinforcing means in order to obtain the desired mechanical characteristics for the thus produced container. In this case, a choice is made of, e.g., metallic materials such as aluminum and stainless steel, usually in the form of a metal lattice or netting. The geometrical shape of the containers is not critical and they can be substantially tetrahedral, substantially octahedral, substantially spherical or any other shape.

According to an advantageous embodiment of the invention, the elements are disposed between said perforated support and a similar perforated device permitting the passage of fluids and whose perforations are sufficiently small to retain said elements between the support and the device. This embodiment makes it possible to reduce the mobility of elements, particularly when they have relatively small dimensions and prevents any segregation between the various elements of the types J and K. The elements generally occupy at least part of the volume of the distillation-reaction zone, i.e., between 1 and 100% and preferably 100% of said volume.

In a particularly advantageous embodiment of the invention, the elements are placed loosely in preferably flexible bags, or in preferably rigid baskets, before being introduced into the distillation-reaction zone. These bags or baskets are made from material in the form of a netting or lattice, whose meshes are sufficiently small to retain the various elements. Preferably the meshes of the bags or baskets are as large as possible so as to limit to the greatest possible extent pressure drop problems. These bags and/or baskets preferably have a size making it possible to easily introduce them through a manhole into the distillation-reaction zone. When using baskets, it is advantageous to use juxtaposed baskets, which then occupy the entire surface of the distallation-reaction zone. These bags and/or baskets are usually stacked in successive layers throughout the height of the distalliation-reaction zone. In the case of baskets having a substantially rectangular cross-section, the stack is preferably produced in such a way that the direction defined by the large side of the rectangle is substantially orthogonal between the individual layers. In the case of a distillation-reaction zone having a substantially circular cross-section, it is possible to use baskets having an adapted shape, so as to occupy the maximum surface of the section.

The distillation-reaction apparatus according to the invention preferably comprises at least two distillation-reaction zones, each containing at least one type J element and at least one type K element, said zones not being in contact with one another, i.e., the apparatus then has between successive distillation-reaction zones zones or empty spaces and/or having trays or liquid redistribution systems and/or distillation zones (e.g., having cap or valve trays, etc.) and/or zones having packing materials, said materials being optionally contained in containers and/or empty containers.

BRIEF DESCRIPTION OF THE DRAWINGS

FIGS. 1,2A,2B,2C,2D,2E,2F,3,4,5A,5C,5E,6A and 6B illustrate the invention without limiting the scope thereof, similar members being given the same reference letters and numerals.

FIG. 1 shows the distillation-reaction apparatus according to the invention.

FIGS. 2a–f illustrates the empty container.

FIG. 3 illustrate the container with the upper and lower bases open.

FIG. 4 illustrates the two half-circumferences.

FIGS. 5a,c,e illustrates the container with catalyst.

FIGS. 6a, b illustrate the basket.

DETAILED DESCRIPTION

FIG. 1 diagrammatically shows part of a distillation-reaction apparatus (1) according to the invention which, in the advantageous embodiment shown therein, has two distillation-reaction zones (H) and (G), a zone (7) containing a liquid redistribution tray (8) and separating the zones (H) and (G) and also a zone (7) surmounting the zone (G). The apparatus is shaped like a substantially cylindrical, vertical column having a substantially constant diameter (d) over the entire column height. Each of the distillation-reaction zones (H) and (G) has loose material on a perforated support (5) (permitting the passage of the upward gaseous flow and the downward liquid flow and retaining the elements $3a,3b,4$) in the case of the embodiment shown in FIG. 1. The type J elements are containers ($3b$) containing granular solid catalytic particles (2). The containers ($3a$) forming the type K2 elements are empty containers and the distillation packing materials (4) form type K1 elements. In the case shown in FIG. 1, the type K1 elements are packing materials which are not identical. The distillation-reaction zone, incorporating the containers ($3a$) and ($3b$) and the packing materials (4), is surmounted by a perforated plate (6) fixed in the column by means not shown in FIG. 1. The elements are introduced into the column by manholes (1) and the plate (6) (or the components necessary for its manufacture) is then installed in the column so as to bring about a maximum limitation of the possible movements of said elements. The supports (5) and the plate (6) are held in place in the column by any adequate means, such as, e.g., catches, not shown in FIG. 1, or by welding.

As shown in FIG. 1, the supports (5) can be associated with a fabric (9) (or a fine grid having openings smaller than those of the support (5), but having an adequate size to permit the passage of the upward gaseous flow and the downward liquid flow), which is fixed by any adequate means to the support (5) or preferably to the apparatus wall. The fabric or grid is generally fixed above the support (5). When using a metal grid, the latter can, e.g., be fixed by welding at the apparatus walls. The use of a fabric or grid is usually only advisable if the openings of the support (5) are too large to retain the elements used. The same arrangement can be adopted for the plates (6), in the case where their openings are too large to retain the elements used, whereby in this case the fabric (9) (or the grid) is preferably fixed below the plates (6).

FIG. 2A is a front sectional view of an empty container ($3a$).

FIG. 2C is a front sectional view of a container ($3c$) containing a packing material (4) and FIG. 2E is that of a container ($3b$) containing solid catalytic particles (2).

FIGS. 2B, 2D and 2F are in each case a sectional view, in a plane perpendicular to the axis yy' and passing through the axis xx', of the container shown respectively in FIGS. 2A, 2C and 2E. These containers have flanges (10) of length (L) (FIGS. 2A,2C and 2E) and thickness (e) (FIGS. 2B,2D and 2F).

FIGS. 3,4,5A,5C and 5E illustrate the stages of manufacturing a container, which can be empty or contain catalytic particles, or a distillation packing material, relative to the invention. In the case shown in FIGS. 2C,2D and 5C, the distillation packing material is cylindrical (e.g. Pall or Raschig ring). For the production of the containers, the starting product is a porous or permeable material tube portion, e.g., of a metal fabric. The cross-section of said tube can be circular, oval or any other shape, so that the tube is referred to hereinafter as "cylindrical or equivalent". In this definition inclusion also takes place of the case where the tube portion is not precisely cylindrical or equivalent, i.e., the edge of the cylinder does not have the same length at all points. This can e.g., be obtained by cutting obliquely and not perpendicularly a longer tube when it is wished to form the tube portion necessary for the production of the container. For the production of containers forming non-empty K2 type elements, the average diameter of the tube used is usually in excess of 1.1 times the diameter of the distillation packing material. The upper and lower bases are initially open (fig. 3). The two half-circumferences (a) and (b) defined by their common ends A and B are moved together until they come into contact and are fixed together, e.g., by welding, whereby said two half-circumferences then form a substantially linear fin or flange ABB'A' (FIG. 4).

In the case of containers forming elements of type J and type K2 which are non-empty, introduction takes place either of the catalytic particles (2), or the distillation packing material (4) (FIGS. 5E and 5C) into the bag, whose bottom has been closed or sealed in the manner described hereinbefore and then the approach and fixing operations are repeated, on this occasion with the half-circumferences defined by their common ends C and D or E and F or any pair of symmetrical points relative to the center of the cross-section of the tube. Both in the case of empty containers and non-empty containers, after fixing, e.g., by welding of the half-circumferences, a substantially linear fin or flange was formed EE'FF' (FIGS. 5A,5C and 5E). The thus obtained containers have two flanges, whose size can be modified. The length L of each of the flanges is respectively equal to AA' or BB' and to EE' or FF'. This length is a function of the width of the weld. Its thickness is approximately twice greater than the thickness of the material constituting the tube. The size of these flanges in accordance with the axis substantially parallel to that defined by the ends AB and EF is substantially equal to the length of each half-circumference which has given rise to it. In the case of the embodiment shown in the drawings, the largest dimension p (FIG. 5C) of the container is substantially equal to the largest dimension of the packing material contained in said container.

FIG. 6A diagrammatically shows in perspective a basket (11) formed from a rigid steel wire having meshes (12), whose sizes are sufficiently small to retain the elements and preferably as large as possible and just small enough to retain the elements. These baskets are filled with elements of different types and are then introduced into the column 1 in the distillation-reaction zone. FIG. 6B diagrammatically shows in a section in a horizontal plane, the distribution of the baskets in the column 1. The shape of each basket is chosen as a function of its position in the column, so that each assembly of baskets occupies the maximum surface.

The present invention also relates to the use of the aforementioned apparatus for performing chemical reactions and for the fractionation of the reaction mixture. In particular, the invention relates to the use of the apparatus for producing ethers by the reaction of olefins having 3 to 8 carbon atoms per molecule with alcohols having 1 to 6 carbon atoms per molecule. As examples of olefins which can be used, reference is made to propylene, isobutylene, or other isomeric butylenes and isoamylene or other isomeric amylanes. As examples of alcohols which can be used, reference is made to methanol, ethanol, n-propanol, isopropanol and butanols. The presently most widely industrially produced ethers are methyl tert. butyl ether (MTBE), ethyl tart. butyl ether (ETBE), isopropyl tert. butyl ether (IFTBE), methyl tert. amyl ether (TAME) and ethyl tert. amyl ether (ETAE).

The invention also relates to the process for the preparation of an ether by the reaction of olefins having 3 to 8 carbon atoms per molecule with alcohols having 1 to 6 carbon atoms per molecule, in the presence of an acid catalyst in the form of solid particles, in which concurrently the reaction and separation by distillation of the products formed during said reaction takes place in an apparatus like that described hereinbefore and which involves the continuous recovery of the ether formed. The most frequently used acid catalyst for performing this reaction is an ion exchange resin in acid form such as, e.g., a sulfonated resin (particularly a sulfonated polystyrene-divinyl benzene resin, such as, e.g., Amberlyst 15 manufactured by Rohm et Haas). Preference is given to the use of olefins having 4 to 6 carbon atoms per molecule and preferably alcohols having 1 to 4 carbon atoms per molecule. Most frequently the olefins used are tertiary olefins.

The conditions for the preparation of ether from at least one olefin and at least one alcohol are standard conditions. Generally a reflux ratio relative to the distillate (i.e., a ratio between the refluxed liquid volume and the drawn off liquid volume) between 0.1:1 and 20:1 and preferably between 0.5:1 and 5:1 is maintained. Most frequently in apparatus (I) use is made of a pressure and temperature range which are as wide as possible, e.g., 100 to 3000 kilopascals (kPa), preferably 200 to 2000 kPa for the pressure and 10° to 200° C. and preferably 40° to 120° C. for the temperature (throughout the apparatus). In each distillation-reaction zone the containers occupy the entire substantially circular cross-section of the distillation-reaction zone. The solid particles contained in the containers forming the type J elements can be given any adequate shape, particularly a substantially cylindrical or spherical shape.

EXAMPLE 1

The determination of the height equivalent to theoretical plate (HETP) makes it possible to characterize the efficiency of a distillation-reaction apparatus from the distillation standpoint. In this example, the HETP was determined by the MacCabe and Thiele method by distilling, with total reflux, a binary methanol-ethanol mixture. At equilibrium, the analysis (refractive index) of the distillate (sample taken at the top of the column) and the residue (sample taken in the boiler) makes it possible to graphically obtain on the basis of the liquid/vapor equilibrium diagram, the number of theoretical plates or trays of the column. The experiments were carried out in a laboratory apparatus in the form of a column having a cylindrical cross-section and an internal diameter of 100 mm, placed on a 10 liter flask (boiler), equipped with a condenser and a reflux system. The apparatus has two thermometers at the top and bottom of the column. The experiments were carried out with total reflux. At thermal equilibrium, a sample is taken in the flask (residue or drawn-off part) and another sample at the top of the column at the reflux level (distillate). The apparatus C1 is filled over a height of 1000 mm with the packing for the reactive column described in EP-B-8860 and shown in its FIGS. 2 and 3. This packing rests on a perforated support, whose circular openings have a diameter of 9 mm. In a C2 apparatus, identical to the C1 apparatus, are introduced in loose form empty containers, Pall rings and containers containing granular catalyst particles in a quantity such that under the conditions of the reaction these particles occupy a volume substantially equal to half the volume of the container containing them. The largest dimension of the containers is 15 mm and the smallest is 12 mm. The Pall rings have a diameter of 15 mm and a height of 15 mm. The envelope of the containers is made from woven polypropylene with square meshes with a side length of 0.3 mm. All the containers have a stainless steel reinforcement. The total height of the bed formed by the containers in the column is 1000 mm. In each of the two experiments, the catalyst quantity in the column, in dry catalyst weight, is identical. The catalyst used is the sulfonated resin sold under the tradename Amberlyst 15 by Rohm & Haas. In the case of apparatus C1 there is a HETP of 0.4 m and in the case of apparatus C2 0.30 m. Therefore the apparatus according to the invention leads to a significant distillation efficiency improvement, because there is a gain of approximately 25% on the height of a theoretical plate.

EXAMPLE 2

In order to simulate the finishing reactor of an industrial unit, MTBE was synthesized in an experimental reactive column. It is supplied by a charge containing methanol and a mixture of butylenes end butanes containing approximately 25% isobutylene already 80% converted into MTBE. The first experiment (I) is carried out with apparatus C1 described in Example 1. In the second experiment (II) illustrating the present invention, use is made of the apparatus C2 described in Example 1. Operating at a pressure of approximately 0.5 Megapascal (MPa), at a temperature between 60° and 80° C. and maintaining a reflux ratio of approximately 1:1, approximately 60% of the residual isobutylene of the first experiment, as compared with approximately 90% in the second experiment is converted into MTBE. Thus, the apparatus according to the invention leads to a much better conversion than in that produced according to EP-B-8860.

We claim:

1. A distillation-reaction apparatus comprising at least one distillation-reaction zone, said zone containing, on a perforated support permitting the passage of fluids, at least one element J comprising a container having an internal volume, vt, and containing a quantity of catalytic solid particles, said particles having a volume, Va, of more than zero but below the internal volume, Vt, of said container, said container having an outer envelope permeable to fluids and impermeable to the solid catalytic particles, and at least one element K having at least the double function of ensuring a predetermined vacuum level in the distillation-reaction zone and ensuring a distillation effect, said vacuum level defined as $(Vt-Va)/Vt$, said elements J and K, alone or in combination, having sufficient mechanical strength to withstand, without excessive deformation, the load of all the elements J and K present in said distillation-reaction zone, and the perforations of said perforated support being smaller than said elements J and K so that the perforated support can retain said elements J and K.

2. An apparatus according to claim 1, wherein the element K comprises distillation packing materials K1 and empty containers or non-empty containers not containing solid catalytic particles K2.

3. An apparatus according to claim 2, wherein the distillation-reaction zone contains the following combinations:
   at least one element J and at least one element K1.

4. An apparatus according to claim 2, wherein the distillation-reaction zone contains the following combination:
   at least one element J and at least one element K2.

5. An apparatus according to claim 2, wherein the distillation-reaction zone contains the following combination:
   at least one element J and at least one element K1 and at least one element K2.

6. An apparatus according to claim 1, wherein at least one container chosen from the group formed from among elements J and elements K has at least one means having the double function of mechanical reinforcement of said container and maintaining a minimum spacing between said container and at least one of the following elements: the closest container in contact with the end of said means or one of the closest solid surfaces in contact with the end of said means.

7. An apparatus according to claim 1 wherein the elements of type J and the elements K occupy at least part of the volume of the distillation-reaction zone between said perforated support and a similar perforated device permitting the passage of fluids and whose perforations are smaller than said elements between said support and said device.

8. An apparatus according to claim 1, wherein elements K have means permitting their separation from elements J by the use of magnetic means.

9. Apparatus according to claim 1, wherein each container containing catalytic particles contains a fluidized bed of said catalytic particles.

10. A distillation-reaction apparatus comprising:
   a reactor containing at least one distillation-reaction zone, said zone containing a perforated support wherein said perforated support permits the passage of fluid,
   at least one catalyst container element, and
   at least one further container element;
   said perforated support being impermeable to said container elements;
   said catalyst container element comprising an outer envelope in which solid catalytic particles are contained, said outer envelope being permeable to fluids but impermeable to said solid catalytic particles, the total volume of said solid catalytic particles being less than the total internal volume of said outer envelope;
   said further container element comprising an outer envelope permeable to fluids, the interior of said outer envelope of said further container element being empty or containing distillation packing materials;

wherein said at least one catalyst container element and said at least one further container element have the ability to withstand, without excessive deformation, the loading of all said container elements in said distillation-reaction zone.

11. An apparatus according to claim 10, wherein said distillation-reaction zone contains at least one of said further container elements wherein the interior of the outer envelope is empty.

12. An apparatus according to claim 10, wherein the said distillation-reaction zone contains at least one of said further container elements wherein said interior of said outer envelope contains distillation packing material.

13. An apparatus according to claim 11, wherein the said distillation-reaction zone contains at least one of said further container elements wherein said interior of said outer envelope contains distillation packing material.

14. An apparatus according to claim 1, comprising a plurality of J elements.

15. An apparatus according to claim 14, wherein the J elements are sufficiently rigid to withstand the weight of the J and K elements without collapsing.

* * * * *